United States Patent [19]

Clusener

[11] Patent Number: 4,548,515
[45] Date of Patent: Oct. 22, 1985

[54] MULTIPLE SENSOR DILATOMETER

[76] Inventor: Gerhard R. Clusener, 112 Reni Rd., Manhasset, N.Y. 11030

[21] Appl. No.: 602,967

[22] Filed: Apr. 23, 1984

[51] Int. Cl.⁴ .......................................... G01N 25/16
[52] U.S. Cl. ...................... 374/56; 336/30; 336/136
[58] Field of Search .............. 374/6, 7, 55, 56, 57; 33/147 D, 148 D; 336/30, 136

[56] References Cited

U.S. PATENT DOCUMENTS

| | | | |
|---|---|---|---|
| 1,489,115 | 4/1924 | Chevenard | 374/55 |
| 3,680,357 | 8/1972 | Clusener | 336/30 |
| 3,885,416 | 5/1975 | Cooper | 374/56 |
| 3,919,879 | 11/1975 | Betz | 374/56 |
| 4,351,615 | 9/1982 | Rodrigues | 374/56 |

*Primary Examiner*—Charles Frankfort
*Assistant Examiner*—Thomas B. Will
*Attorney, Agent, or Firm*—Burton E. Levin

[57] ABSTRACT

Dilatometers are described which employ measuring heads having multiple linear variable differential transformer dilation sensors for concurrently measuring the thermal dilation of multiple specimens within a single conventional electric tube furnace. The sensors, which have their cores coupled to calibrating micrometers, are positioned in a closely separated cluster in which each sensor is parallel, abreast and adjacent to each other. Separate parallel pushrods, which abut separate specimens within a common tubular specimen holder, are attached to the axially mobile coil of each sensor at the point closest to the center of the cluster. The resulting close separation of the parallel pushrods and their specimens within a small diameter specimen holder permits the use of an energy efficient electric tube furnace having a small diameter oriface and facilitates uniform heating of the pushrods and specimens. The capacity of such dilatometers to handle large numbers of specimens in a short period, as is often required for production control purposes, can be further enhanced by employing two such measuring heads with their pushrods and specimen holders being inserted into opposite ends of the oriface of the tube furnace.

18 Claims, 6 Drawing Figures

MULTIPLE SENSOR DILATOMETER

BACKGROUND OF THE INVENTION

1. Field of the Invention

This invention relates generally to dilatometers and, more particularly, to dilatometers having multiple linear variable differential transformer dilation sensors for making independent measurements on multiple specimens which are subjected to identical temperatures and rates of temperature change within a common furnace. Such multiple sensor dilatometers can handle large numbers of specimens in a short period and are especially suited for production control purposes.

2. Description of the Prior Art

Dilatometers are analytical instruments that respond to the linear thermal expansion or contraction of solids. Typically, these instruments have a variable temperature furnace in which the test specimen rests between a flat surface on a stationary object and an opposing flat surface on a movable object, such as a ceramic pushrod, that extends outside the furnace. Temperature induced changes in the length of the specimen are transmitted through the rod to a mechanical, optical or electrical system for amplifying and measuring that change. These instruments can be used to make precise measurements of changes in length resulting from small temperature changes or to plot variations in the rate of linear expansion or contraction over a broad temperature range.

Among the least sophisticated dilatometers in common use are those in which the push rod is coupled to a dial gauge and the dilation of a specimen is read directly from that gauge. Such dial gauge dilatometers are simple to use and inexpensive, but generally are suitable only for low to moderate temperature applications that do not demand great precision.

U.S. Pat. No. 3,680,357 describes a far more precise type of dilatometer in which the dilation sensor is a linear variable differential transformer which translates specimen dilation into electrical signals that can readily be amplified and recorded. In such sensor, the core floats freely in the coil and each of these elements is separately supported at its ends by a pair of compound cantilevered flat springs. These springs permit independent and frictionless axial movement of the suspended element, but restrain radial or transverse movement. This independent and frictionless axial mobility of the core and coil facilitates calibration of the sensor and renders it extremely sensitive to minute changes in specimen length, thereby making possible exceptionally accurate measurements of thermally induced expansion or contraction.

When such dilatometer is used with a single pushrod, as shown in FIG. 1 of the aforementioned Patent, that pushrod commonly is coupled to and supported only by the core of the linear variabe differential transformer and it extends into the open end of a tubular specimen holder, where it abuts a specimen that is held between a flat ground surface at the end of the pushrod and a similar flat ground surface on the interior of the other closed end of the specimen holder. An opening commonly is provided in the wall of the specimen holder adjacent to its closed end to facilitate specimen changes. The closed end of the specimen holder is inserted into a variable temperature furnace, which, for many applications, is a conventional electric tube furnace.

For measurements of the differential thermal expansion of two specimens, separate closely spaced pushrods may be coupled to the core and coil of the linear variable differential transformer and the equally closely spaced specimens are held abreast within a single tubular specimen holder that is inserted in a similar electric tube furnace, as shown by U.S. Pat. No. 3,898,836.

Since a significant amount of heat is lost through the open ends of the oriface of an electric tube furnace, it is usually advantageous to have an oriface of as small diameter as practical in order to minimize furnace temperature gradients and power consumption. The use of such small oriface furnace does, however, restrict the maximum diameter of the specimen holder, which, in turn, limits the maximum diameter of both the specimen and pushrod. The maximum diameter of the specimen holder may be further restricted when furnace temperatures are very high and it becomes necessary to protect the specimen and sensor from oxidation by placing them within an evacuated enclosure. Typically, such evacuated enclosure includes a closed end protective tube that surrounds the specimen holder and that also must fit into the oriface of the electric tube furnace.

In order to take advantage of the moderate acquisition cost, internal temperature uniformity and economy of operating an electric tube furnace having a small oriface, dilatometer specimens, pushrods, specimen holders and protective tubes generally have been reduced to as small diameter as is practical without sacrificing structural integrity and ease of handling. In the case of two pushrod differential dilatometers, another practical limitation on diameter reductions of the specimen holder and protective tube has been the distance between the pushrod couplings on the core and coil of the linear variable differential transformer.

Largely as a result of such diameter reductions, highly accurate and power efficient dilatometers now are available which employ linear variable differential transformer sensors and conventional electric tube furnaces having small orifaces. These are widely used for research purposes and are invaluable in studying the compatibility under changing temperature conditions of different materials which are bonded together or are in close contact; e.g., metal to glass, enamel to substrates, thin film deposits in microcircuits or metal or plastic fillings in natural teeth. They also have been utilized to detect phase changes occurring during the heating or cooling of materials, such as steel, and to study the effect of different heating or cooling rates on the physical properties of those materials.

They are, however, not as widely utilized for production control or other applications that involve repetitive measurements with a single pushrod sensor on large numbers of specimens which must be subjected to identical temperatures and rates of temperature change. Since an individual measurement may require up to several hours or more, a conventional single sensor dilatometer and furnace, which measures the dilation of a single specimen at a time, simply is too slow for most production control requirements. The use of multiple single sensor dilatometers with individual furnaces is unattractive both because of cost and the difficulty of identically controlling different furnaces. The use of multiple single sensor dilatometers with a single furnace is similarly unattractive because an electric tube furnace having an oriface large enough to accomodate the multiple protective tubes and specimen holders of such dilatometers is otherwise unnecessarily large and its excessive internal temperature gradients make it very difficult to subject the widely spaced specimens to identical temperatures and heating rates.

It is the broad object of this invention to provide an dilatometer that is capable of concurrently measuring the thermal expansion or contraction of multiple specimens within a single energy efficient furnace, thereby making it suitable for production control purposes. A specific object of this invention is to provide such multisensor dilatometer that employs linear variable differential transformer dilation sensors, each of which has a single pushrod coupled to its coil. It is a further specific object to provide such dilatometer in which the coils of at least two sensors are closely positioned abreast and are coupled to separate closely positioned parallel pushrods which are adapted to abut separate specimens held within a single specimen holder. Another specific object is to provide such dilatometer in which at least four specimens can be uniformly heated within an electric tube furnace having a small diameter oriface and internal temperature gradient. Still another specific object is to provide a compact unitary dilatometer measuring head having multiple linear variable differential transformer dilation sensors that are closely positioned abreast, that can readily be calibrated and in which the coils exhibit independent frictionless axial mobility, but are laterally restrained.

These objects and other advantages which will be apparent from this specification, are achieved by the invention described below.

It has now been determined that accurate measurements of dilation can be made with a single pushrod that is coupled to the coil, rather than the core, of a linear variable differential transformer sensor and that such coupling permits exceptionally close spacing of the pushrods from multiple sensors. Broadly, my invention is an energy efficient single furnace dilatometer having multiple linear variable differential transformer dilation sensors in which the pushrods are coupled to closely spaced coils and which, therefore, is capable of concurrently measuring the thermal expansion or contraction of multiple closely spaced specimens under substantially identical conditions in a single energy efficient furnace.

One aspect of this invention is such dilatometer comprising (a) a measuring head in which at least two linear variable differential transformer dilation sensors are positioned in a closely spaced apart cluster so that each sensor is parallel to, abreast of and adjacent to each other sensor, the coil of each sensor is axially movable by and supports an end of a separate tandemly positioned pushrod, the other end of that pushrod is adapted to abut a flat surface on a separate specimen, and each pushrod and its supporting coil is coupled at a position on that coil closest to the axis of the cluster of sensors so that all the pushrods are positioned parallel, abreast and closely spaced apart, (b) a tubular specimen holder having an open end, into which the specimen abutting ends of the pushrods extend, and a closed end that is internally adapted to abut another flat parallel surface on each specimen and (c) an electric tube furnace into which the closed end of the specimen holder extends.

Preferred embodiments of this aspect of the invention include dilatometers in which from two to four sensors are employed in the measuring head and dilatometers in which two measuring heads are employed with their associated push rods and specimen holders extending into opposite ends of the oriface in an electric tube furnace.

Another aspect of this invention is a measuring head for such dilatometer which has at least two linear variable differential transformer dilation sensors with axially movable coils. These sensors are positioned in a closely spaced apart cluster in which each sensor is adjacent, parallel and abreast of each other sensor and each coil bears a separate coupling means which is positioned on that coil proximate to the axis of the cluster of sensors and which is adapted for engaging an end of a separate pushrod and supporting that pushrod parallel to and in tandem with its coupled coil.

Preferred embodiments of this aspect of the invention include measuring heads having two to four sensors, measuring heads in which the cores of the sensors are attached to a single yoke on which a single micrometer bears to axially move all of the cores for calibration purposes, measuring heads in which each core is supported by a pair of compound cantilevered flat springs, measuring heads in which each core is moved axially by a separate calibrating micrometer and measuring heads in which each core is supported by a separate calibrating micrometer.

An especially preferred embodiment of this aspect of the invention is a dilatometer measuring head in which the core floats freely in the coil of each of two linear variable differential transformer dilation sensors that are positioned parallel, abreast and closely spaced from each other, each core is axially movable by a calibrating micrometer, each coil is supported by and axially movable on a pair of compound cantilevered flat springs and each coil is attached to a separate coupling means that is positioned on that coil proximate to the other coil and that is adapted to engage an end of a separate pushrod and support that pushrod parallel to and in tandem with the coil to which it is coupled.

DESCRIPTION OF THE PREFERRED EMBODIMENTS

Figure 1:
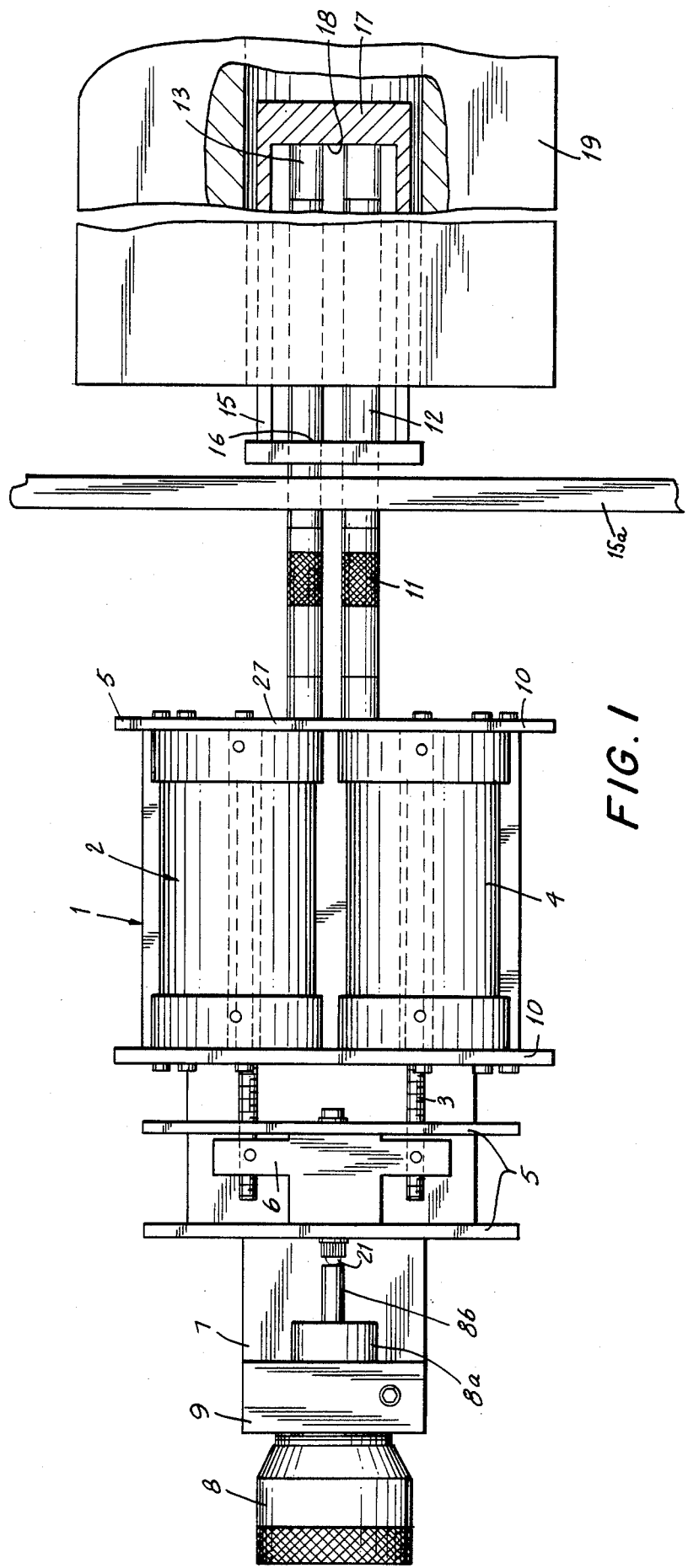
FIG. 1 is a partial plan view, partially cut away, of a dilatometer of this invention in which the measuring head has two linear variable differential transformer dilation sensors and a single calibrating micrometer.

FIG. 1 illustrates a dilatometer of this invention which employs a measuring head 1 (shown also in FIG. 2) having two linear variable differential transformer dilation sensors 2. The sensors 2 are positioned parallel and abreast of each other and advantageously are positioned as close together as possible without danger of touching. The core 3 of each sensor floats freely in coil 4 and is threaded through yoke 6. This threaded attachment permits small axial movement of the core and facilitates electrical zeroing of the sensor.

Figure 3:
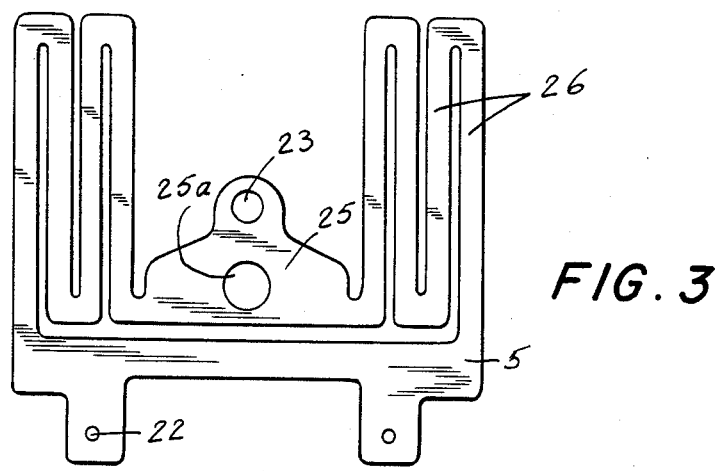
FIG. 3 is a partial cross section along line B—B of FIG. 1 showing a plan view of one of the springs supporting the sensor cores.

Yoke 6 is supported by a pair of compound cantilevered springs 5 which are attached to a base 7. Each of these springs 5, one of which is more clearly shown in FIG. 3, is mounted on base 7 by screws passing through holes 22 and holds yoke 6 by a screw passing through hole 23 in cantilevered central leg 25, which is rendered less rigid by void 25a. The accordion-like interaction of cantilevered central leg 25 and cantilevered lateral legs 26 in the pair of springs 5 provides frictionless axial mobility to cores 3 and restrains lateral movement. Thus, when micrometer 8, which is held at its neck 8a by bracket 9 attached to base 7, is turned so as to bring its stem 8b to bear on anvil 21 on yoke 6, cores 3 can be displaced as a group by a precisely measured distance relative to their stationary coils 4, thus simplifying calibration of the sensors.

Coils 4 also are supported at their ends by a pair of compound cantilevered springs 10, which are attached to base 7 and which similarly provide frictionless axial mobility to the coils 4 while restraining their lateral movement. One such spring 10 is more clearly shown in FIG. 4. It is mounted on base 7 by screws passing through holes 22 and holds a coil 4 on each cantilevered central leg 25 by screws passing through holes 24. As in the core supporting spring 5, each of the cantilevered central legs 25 of coil supporting spring 10 is contiguous with cantilevered lateral legs 26. Each also has a void 25a, which provides access to the core, and an additional hole 27 to accomodate a pushrod engaging sleeve 11.

Figure 2:
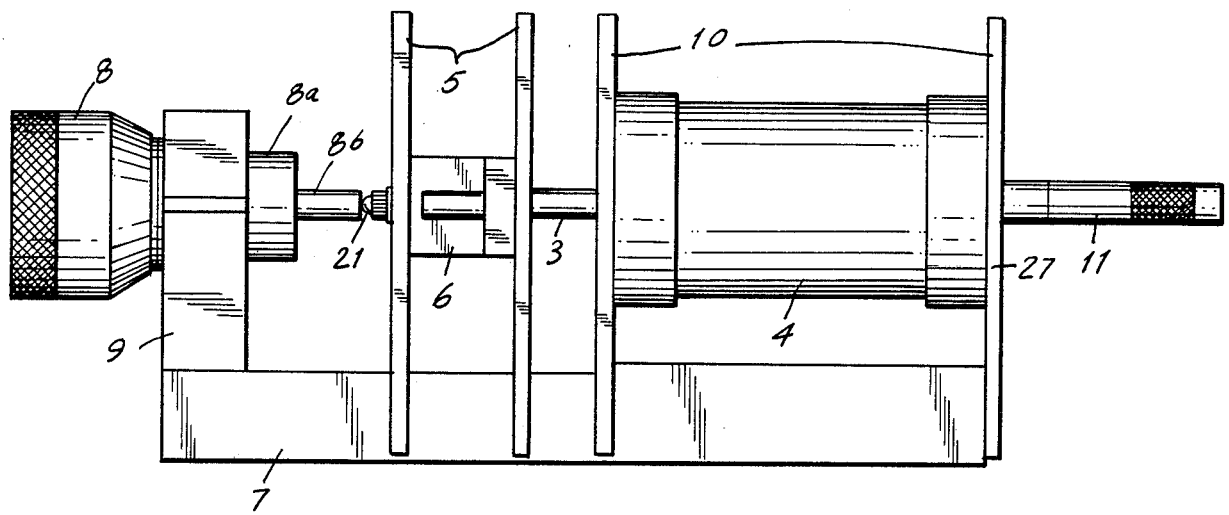
FIG. 2 is a side elevation view of the measuring head shown in FIG. 1.

As more clearly shown in FIGS. 1 and 2, each coil 4 is attached to a sleeve 11 which extends through hole 27 in a central leg 25 and into which a pushrod 12 is inserted and held by friction. For high temperature applications, pushrods 12 advantageously are made of a heat resistant material, such as alumina or fused silica. Sleeve 11 is positioned on each coil 4 at the point closest to the axis of the pair of coils (i.e., closest to the other adjacent coil 4), thus placing each pushrod 12 in close proximity to the other.

Each of pushrods 12 passes loosely through a separate hole in post 15a which is attached to base 7, and extends into the open end 16 of a tubular specimen holder 15 where it abuts a separate specimen 13 that is held between that pushrod and the interior surface of the closed end 17 of specimen holder 15. Specimen holder 15, which for high temperature applications advantageously is made of alumina or fused silica, is rigidly held at its open end 16 by any suitable clamp (not shown) that is attached to post 14. The closed end 17 of specimen holder 15, along with specimens 13 and the abutting ends of pushrods 12, is inserted into one end of the oriface of a conventional electric tube furnace 19 which rests on base 7.

Since the inside diameter of specimen holder 15 need be only large enough to accomodate and permit frictionless movement of pushrods 12, and its wall need only be sufficiently thick to provide rigidity, the close spacing of the pushrods which is made possible by this measuring head design permits dilation measurements to be made concurrently on multiple specimens without enlarging the furnace oriface, which would lead to greater heat loss through its open ends and would increase the internal furnace temperature gradients. The close spacing of pushrods and specimens also minimizes the effect of any small gradients that may exist.

An especially preferred embodiment of this invention is an addition to the dilatometer of FIG. 1 which permits concurrent dilation measurements to be made on four specimens. In this embodiment, a second measuring head 1, along with a second specimen holder 15 and a second pair of pushrods 12, are positioned at the opposite end of electric tube furnace 19 with that second specimen holder being inserted into the oriface of the furnace from that opposite end.

Figure 5:
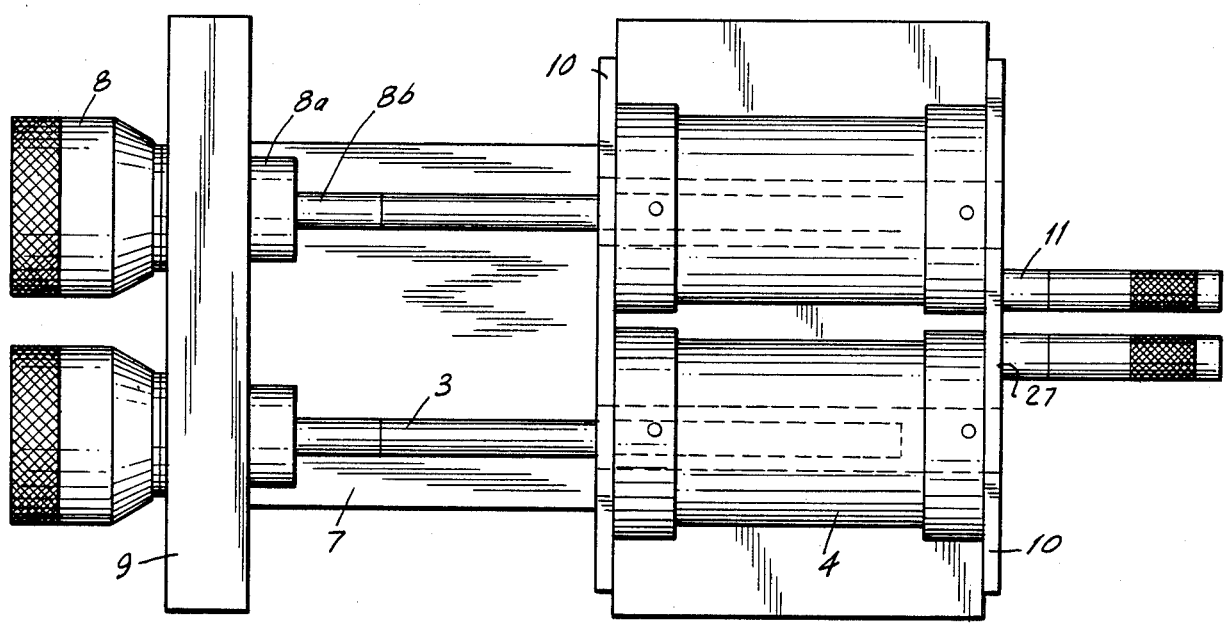
FIG. 5 is a plan view of another measuring head of this invention which employs separate calibrating micrometers for the linear variable differential transformer dilation sensors.

FIG. 5 illustrates a modification of the measuring head of FIGS. 1 and 2 which permits separate calibration of the sensors. As in the measuring head embodiment described above, the coils 4 of the linear variable differential transformer dilation sensors are held close together by a pair of compound cantilevered flat springs 10 which are mounted on base 7. Similarly, each coil 4 bears a pushrod engaging sleeve 11 which extends from a point on that coil which is adjacent to the other coil 4, thus assuring close spacing of the pushrods (not shown). Unlike the measuring head of FIGS. 1 and 2, each core 3 of this embodiment is directly attached to and axially movable by the stem 8b of a separate micrometer 8, both micrometers being held at their necks 8a by micrometer bracket 9 which is mounted on base 7. Since each core 3 is both supported and axially movable by the stem 8b of a rigidly held micrometer 8, neither the yoke 6 nor the core supporting springs 5 of the earlier described measuring head are necessary here and accordingly are omitted.

Although the measuring heads that are specifically illustrated above have only two linear variable differential transformer dilation sensors shown for reasons of clarity, it should be apparent that it is possible to retain the described benefit of closely spaced pushrods in a common small diameter specimen holder when as many as four or more such sensors are positioned in a closely spaced apart cluster in which all the sensors are parallel, adjacent and abreast. As used in this specification to describe the sensors in such clusters, the term "adjacent" means that no two sensors are separated by a third. In these clusters, the sensors advantageously are positioned at equal distances from the center or axis of the cluster.

Figure 4:
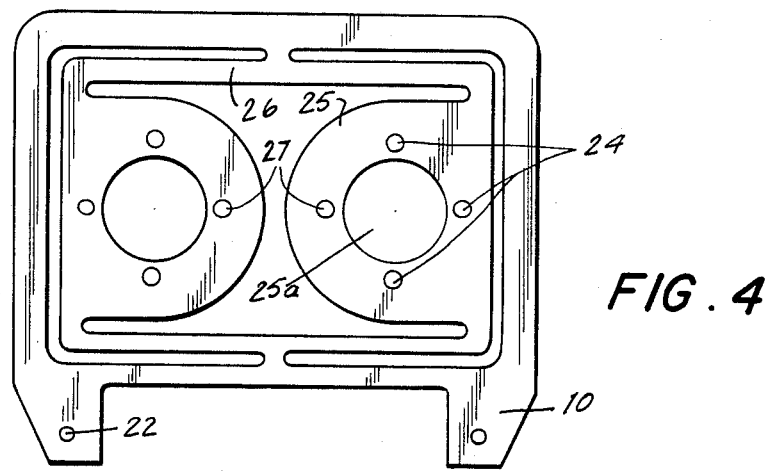
FIG. 4 is a partial cross section along line A—A of FIG. 1 showing a plan view of one of the springs supporting the sensor coils.
Figure 6:
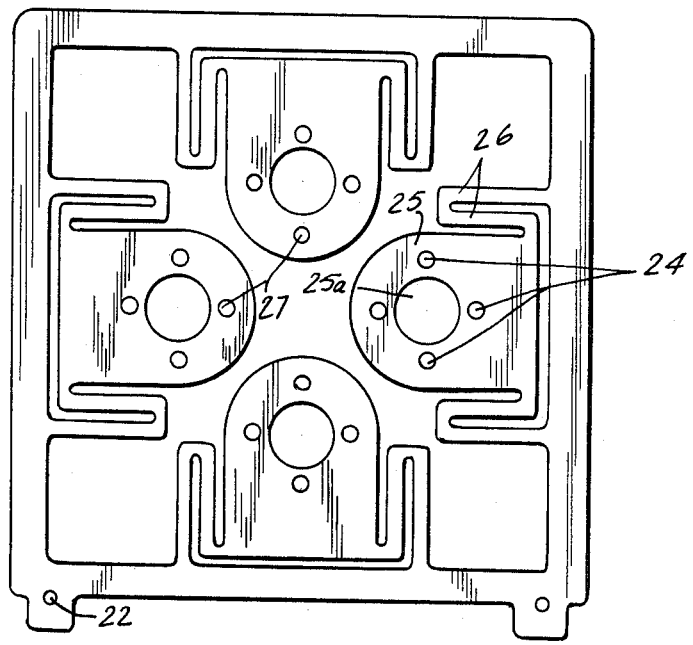
FIG. 6 is a plan view of a spring for supporting the ends of four linear variable differential transformer dilation sensor coils in a measuring head of this invention.

FIG. 6 illustrates a modification of the compound cantilevered flat spring 10 of FIG. 4 that is suitable for deployment at both ends of the coils of four such closely spaced sensors, thereby increasing the capacity of the above illustrated measuring heads. Like earlier described spring 10, this spring can be mounted to a base, such as base 7, by screws passing through holes 22. Each central cantilevered leg 25 has a core accessing void 25a and is attached to an end of a sensor coil by screws passing through holes 24. The interaction of each central cantilevered leg 25 with the contiguous lateral cantilevered legs 26 provides frictionless axial mobility to the supported coil. The pushrod engaging sleeve which is attached to each coil extends through hole 27 in a central leg 25. As in earlier described spring 10, the pushrod engaging sleeve is attached to each coil at a position closest to the other coils, thus minimizing the space required in a specimen holder for the cluster of pushrods.

It will, of course, be understood that various other additions and modifications may be made in the embodiments of this invention described above without departing from the spirit and scope of the invention as defined in the claims below.

The embodiments of the invention in which an exclusive property or privilege is claimed are defined as follows:

1. Dilatometer comprising
(a) a measuring head having at least two independently operating linear variable differential transformer dilation sensors which are positioned in a closely spaced apart cluster, each said sensor being parallel, abreast and adjacent to each other, the coil of each said sensor being axially movable by and supporting an end of a separate tandemly positioned pushrod, the other end of said pushrod being adapted to abut a flat surface on a separate specimen, and each said pushrod and its supporting coil being coupled at a position on said coil proximate to the axis of said cluster of sensors so that all said pushrods are positioned parallel, abreast and closely spaced apart,
(b) a tubular specimen holder having an open end, into which the specimen abutting end of each said pushrod extends, and a closed end that is internally adapted to abut another flat parallel surface on said specimen and
(c) a furnace into which the closed end of said specimen holder extends.

2. Dilatometer of claim 1 wherein two said sensors are employed in said measuring head.

3. Dilatometer of claim 1 wherein four said sensors are employed in said measuring head.

4. Dilatometer of claim 1 wherein said furnace is an electric tube furnace having an oriface that is open at both ends.

5. Dilatometer of claim 4 wherein said furnace is positioned intermediate two said measuring heads and specimen holders, said specimen holders being inserted onto opposite open ends of said oriface.

6. Dilatometer measuring head comprising at least two independently operating linear variable differential transformer dilation sensors having axially movable coils, said sensors being positioned in a closely spaced apart cluster in which each said sensor is adjacent, parallel and abreast of each other said sensor, each said coil having separate coupling means positioned thereon proximate to the axis of said cluster of sensors and each said coupling means being adapted for engaging an end of a separate pushrod and supporting said pushrod parallel to and in tandem with its coupled coil.

7. Dilatometer measuring head of claim 6 wherein each said coil is supported at its ends and is axially movable on a pair of compound cantilevered flat springs.

8. Dilatometer measuring head of claim 6 wherein the cores of said sensors are axially movable by calibrating means.

9. Dilatometer measuring head of claim 8 wherein each said core is axially movable by a separate said calibrating means.

10. Dilatometer measuring head of claim 9 wherein each said core is attached to and supported by a separate said calibrating means.

11. Dilatometer measuring head of claim 8 wherein all said cores are attached to a yoke which is movable by a single said calibrating means.

12. Dilatometer measuring head of claim 11 wherein said yoke is supported by a pair of compound cantilevered flat springs which permit axial movement of said cores.

13. Dilatometer measuring head of claim 8 wherein said calibrating means is a micrometer.

14. Dilatometer measuring head comprising two independently operating linear variable differential transformer dilation sensors in each of which the core floats freely in the coil, said sensors being positioned parallel, abreast and closely spaced apart, each said core being axially movable by a calibrating micrometer, each said coil being supported by and axially movable on a pair of compound cantilevered flat springs and each said coil bearing separate coupling means positioned thereon proximate to the coil of the other said sensor, each said coupling means being adapted for engaging an end of a separate pushrod and supporting said pushrod parallel to and in tandem with its coupled coil.

15. Dilatometer measuring head of claim 14 wherein each said core is attached to and supported by a separate said calibrating micrometer.

16. Dilatometer measuring head of claim 14 wherein both said cores are attached to a yoke that is supported by a pair of compound cantilevered flat springs and that is movable by a single said calibrating micrometer.

17. Dilatometer measuring head of claim 16 wherein each said core is attached to said yoke by separate adjustable attachment means that permits axial movement of said core relative to said yoke.

18. Dilatometer measuring head of claim 17 wherein said adjustable attachment means is an axial extension of said core which is threaded into said yoke.

* * * * *